US008420682B2

(12) United States Patent
Poinsard et al.

(10) Patent No.: US 8,420,682 B2
(45) Date of Patent: Apr. 16, 2013

(54) N-PHENYLACETAMIDE DERIVATIVES, WHICH INHIBIT THE ENZYME SOAT-1, AND PHARMACEUTICAL AND COSMETIC COMPOSITIONS CONTAINING THEM

(75) Inventors: Cédric Poinsard, Le Plan de Grasse (FR); Thibaud Portal, Opio (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 13/202,732

(22) PCT Filed: Feb. 26, 2010

(86) PCT No.: PCT/EP2010/052494
§ 371 (c)(1),
(2), (4) Date: Oct. 11, 2011

(87) PCT Pub. No.: WO2010/097464
PCT Pub. Date: Sep. 2, 2010

(65) Prior Publication Data
US 2012/0021017 A1  Jan. 26, 2012

Related U.S. Application Data

(60) Provisional application No. 61/202,419, filed on Feb. 26, 2009.

(30) Foreign Application Priority Data

Jun. 5, 2009  (FR) ...................................... 09 53752

(51) Int. Cl.
A61K 31/4166 (2006.01)
C07D 233/78 (2006.01)

(52) U.S. Cl.
USPC ....................................... 514/386; 548/311.1

(58) Field of Classification Search ............... 548/311.1; 514/386
See application file for complete search history.

(56) References Cited

U.S. PATENT DOCUMENTS

| 4,623,663 A | 11/1986 | Pittz et al. |
| 5,003,106 A | 3/1991 | De Vries |
| 5,106,873 A | 4/1992 | O'Brien et al. |
| 5,338,849 A | 8/1994 | Festal et al. |
| 6,133,326 A | 10/2000 | Mayne |
| 6,271,268 B1 | 8/2001 | Mayne |
| 2007/0197617 A1 | 8/2007 | Chen et al. |
| 2010/0247583 A1 | 9/2010 | Portal et al. |
| 2010/0273813 A1 | 10/2010 | Portal |

FOREIGN PATENT DOCUMENTS

| DE | 1032258 | 6/1958 |
| EP | 0293880 A1 | 12/1988 |
| EP | 0370740 A1 | 5/1990 |
| EP | 0424194 A2 | 4/1991 |
| EP | 0433662 A2 | 6/1991 |
| EP | 0577171 A1 | 8/1993 |
| WO | WO 96/10559 | 4/1996 |
| WO | WO 2005/034931 A1 | 4/2005 |
| WO | WO 2009/030747 A1 | 3/2009 |
| WO | WO 2009/030750 A1 | 3/2009 |
| WO | WO-2009/030747 A1 * | 12/2009 |

OTHER PUBLICATIONS

Rajesh K. Kharbanda et al., "Systemic Acyl-CoA:Cholesterol Acyltransferase Inhibition Reduces Inflammation and Improves Vascular Function in Hypercholoesterolemia", Circulation, 2005, vol. 11, pp. 804-807.
Luigi Puglielli et al., "Alzheimer's Disease: The Cholesterol Connection", Nature Neuroscience, vol. 6, No. 4, Apr. 2003, pp. 345-351.
Tapio Nikkari, "Comparative Chemistry of Sebum", The Journal of Investigative Dermatology, vol. 62, No. 3, 1974, pp. 257-266.
P.H. Stahl and C.G. Wermuth, "Handbook of Pharmaceutical Salts: Properties, Selection and Use", Wiley-VCH, 2002.
B. Dundar et al., "Synthesis and Antioxidative Properties of Novel Thiazolidinedione/Imidazolidinedione Compounds as Retinoids", Pharmazie, vol. 57, No. 7, 2002, pp. 438-441.
Mario Pinza et al., "Systhesis and Pharmacological Activity of a Series of Dihydro-1H-Pyrrolo[1,2,α]Imidazole-2,5(3H,6H)-Diones, a Novel Class of Potent Cognition Enhancers", J. Med. Chem., 1993, vol. 36, pp. 4214-4220.
P. Coudert et al., "Synthese Et Evaluation de L'Activite Sur Le Systeme Nerveux Central De Nouvelles Triaza-Spirodecanediones", Pharm. Acta Helv. vol. 66, No. 5-6, 1991, pp. 155-159.
Cyril O. Usifoh, "Anticonvulsant Activity of Reation Products of 5,5-Diphenylhydantoin With Sustituted Methylene Bromides", Arch. Pharm. Med. Chem., 2001, vol. 334, pp. 366-368.
Kiyoshi Matsumoto et al., "Multicomponent STRECKER Reaction Under High Pressure", Helvetica Chimica Acta, vol. 88, 2005, pp. 1734-1753.
Marcelo J. Nieto et al., "Solution-Phase Parallel Synthesis of Spirohydantoins", J. Comb. Chem., 2005, vol. 7, pp. 258-263.

(Continued)

Primary Examiner — Kamal Saeed
Assistant Examiner — Janet L Coppins
(74) Attorney, Agent, or Firm — SNR Denton US LLP

(57) ABSTRACT

Compounds of general Formula (I),

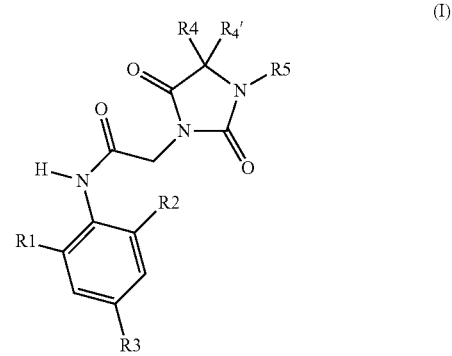

and cosmetic and pharmaceutical compositions including such a compound are described.

23 Claims, No Drawings

OTHER PUBLICATIONS

Yann Davion et al., "Systhesis of Substituted 1,4-Benzoxazepin-3-One Derivatives", Heterocycles, vol. 63, No. 5, 2004, pp. 1093-1112.

Eusebio Juaristi et al., "Enantioselective Synthesis of α-Amino Acids From Chiral 1-4-Benzodiazepine-2,5-Diones Containing the α-Phenethyl Group", J. Org. Chem., 1999, vol. 64, pp. 2914-2918.

"Protective Groups in Organic Chemistry", published by McOmie J.W.F., Plenum Press, 1973, in "Protective Groups in Organic Synthesis", 2nd edition, Greene T.W. and Wuts P.G.M., published by John Wiley & Sons, 1991, and in "Protecting Groups", Kocienski P.J., 1994, Georg Thieme Verlag.

International Search Report (PCT/ISA/210) issued on May 27, 2010, by European Patent Office as the International Searching Authority for International Application No. PCT/EP2010/052494.

A. White et al., "Heterocyclic Amides: Inhibitors of Acyl-CoA: Cholesterol $O$-Acyl Transferase with Hypocholesterolemic Activity in Several Species and Antiatherosclerotic Activity in the Rabbit", J. Med. Chem., Jan. 1, 1996, pp. 3908-3919, vol. 39.

P. O'Brien et al., Inhibitors of Acyl-CoA: Cholesterol $O$-Acyltransferase. Synthesis and Pharmacological Activity of (±)-2-Dodecy-α-phenyl-$N$-(2,4,6-trimethoxyphenyl)-2$H$-tetrazole-5-acetamide and Structurally Related Tetrazole Amide Derivates, J. Chem, Jan. 1, 1996, pp. 2354-2366, vol. 39, No. 12.

\* cited by examiner

N-PHENYLACETAMIDE DERIVATIVES, WHICH INHIBIT THE ENZYME SOAT-1, AND PHARMACEUTICAL AND COSMETIC COMPOSITIONS CONTAINING THEM

This application is the United States national phase of PCT/EP2010/052494, filed Feb. 26, 2010, and designating the United States (published in the English language on Sep. 2, 2010, as WO 2010/097464 A1; the title and abstract were also published in English), which claims priority under 35 U.S.C. §119 of FR 0953752, filed Jun. 5, 2009, and also claims benefit under 35 U.S.C. §119(e) of U.S. Provisional Application No. 61/202,419 filed Feb. 26, 2009, each hereby expressly incorporated by reference in its entirety and each assigned to the assignee hereof.

The invention relates to novel N-phenylacetamide derivatives, which are inhibitors of the enzyme SOAT-1 (Sterol-O-Acyl Transferase-1, also known as ACAT-1: Acyl-coenzyme A Cholesterol Acyl Transferase). The invention also relates to the use of these derivatives in pharmaceutical compositions intended for use in human or veterinary medicine, or alternatively in cosmetic compositions, and also to their non-therapeutic use.

Compositions with activity of SOAT-1-inhibiting type are widely described in the literature as having activity in regulating biological processes involving cholesterol and derivatives thereof. These properties give this class of compounds strong potential in the treatment or prevention of many pathologies, and more particularly in dermatology and in cardiovascular diseases or central nervous system complaints. Most of the biological effects of SOAT-1 inhibitors are mediated by prevention of the synthesis of cholesterol esters by the enzyme SOAT-1. Among the prior art documents describing SOAT-1-inhibiting molecules, mention may be made, for example, of WO 96/10559, EP 0 370 740, EP 0 424 194, U.S. Pat. No. 4,623,663, EP 0 557 171, U.S. Pat. No. 5,003,106, EP 0 293 880, EP 0 433 662 and U.S. Pat. No. 5,106,873, which describe compounds for treating arteriosclerosis or hypercholesterolaemia. The therapeutic potential of SOAT-1 inhibitors in the treatment of cardiovascular diseases, and in particular of hypercholesterolaemia and arteriosclerosis, is also described by Kharbanda R. K. et al., in *Circulation*, 2005, 11, 804. The potential of SOAT-1 inhibitors for the treatment of Alzheimer's disease has also been reported in the literature, for example by Puglielli, L. et al., in *Nature Neurosciences* 2003, 6 (4), 345.

U.S. Pat. No. 6,133,326, U.S. Pat. No. 6,271,268 and WO 2005/034 931 describe SOAT-1-inhibiting compounds for inhibiting the production of sebum. In the field of dermatology, in particular, it is particularly advantageous to prevent excessive sebum production and all the associated conditions. Sebum is produced by the sebaceous glands. The largest concentration of sebaceous glands is found on the face, the shoulders, the back and the scalp. Sebum is secreted at the surface of the skin, where it plays a major physiological role, associated with maintaining the skin barrier and a microenvironment that permits regulation of the cutaneous bacterial and fungal flora.

Sebum hyperproduction is usually associated with a skin or scalp of greasy appearance, which is a cause of discomfort and of degraded appearance. Moreover, sebum hyperproduction may give rise to seborrhoeic dermatitis and is associated with an increased incidence or worsening of acne. The cholesterol esters produced in the sebaceous glands by SOAT-1 are one of the components of sebum, among several classes of lipids including triglycerides, wax esters and squalenes, as described by Nikkari, T., in *J. Invest. Derm.* 1974, 62, 257. Inhibition of this enzyme or of other acyl transferases may thus make it possible to inhibit sebum production. U.S. Pat. No. 6,133,326 especially describes the inhibition of sebum with ACAT-1 (also known as SOAT-1) inhibitors. However, at the present time, no treatment using such inhibitors is commercially available. The only treatments that can remedy or relieve hyperseborrhoea-related disorders are systemic hormonal treatments or systemic treatment with 13-cis-retinoic acid, the side effects of which treatments greatly limit their field of application. There is thus a clear medical and cosmetic need to treat complaints and pathologies related to sebum hyperproduction.

In this context, the present invention proposes to provide novel N-phenylacetamide derivatives that are powerful inhibitors of the enzyme SOAT-1.

One subject of the invention is novel N-phenylacetamide derivatives, which are inhibitors of the enzyme SOAT-1, and which correspond to the general formula (I) below:

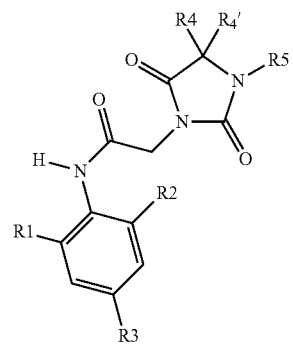

in which:

$R_1$ represents a group $C_{1-6}$ alkyl, $C_{3-7}$ cycloalkyl, $C_{1-6}$ alkyloxy, $C_{1-6}$ fluoroalkyl or $C_{1-6}$ fluoroalkyloxy or a group —$(CH_2)_n$—$C_{3-7}$ cycloalkyl, $R_2$ and $R_3$ are identical or different and represent a hydrogen, fluorine, chlorine, bromine or iodine atom or a group $C_{1-6}$ alkyl, $C_{3-6}$ cycloalkyl, $C_{1-6}$ alkylthio, $C_{1-6}$ alkyloxy, $C_{1-6}$ fluoroalkyl or $C_{1-6}$ fluoroalkyloxy or a group —$(CH_2)_n$—$C_{3-7}$ cycloalkyl, $R_4$ and $R_4'$ are identical or different and represent a group $C_{1-6}$ cycloalkyl, a group —$(CH_2)_n$—$C_{3-7}$ cycloalkyl or a group $C_{1-6}$ alkyl optionally substituted with one to three groups $R_a$, or the groups $R_4$ and $R_4'$ form, with the carbon atom that bears them, a ring $C_{1-6}$ alkyl, $R_5$ represents a group chosen from:
  a phenyl group substituted with at least one, two or three identical or different substituents chosen from the groups $S(O)_p$, $COOR_b$ and CN and optionally accompanied by a group Ra,
  a group —$(CH_2)_n$-aryl, the aryl group being substituted with one or more groups $S(O)_p$, $COOR_a$ or CN, $R_a$ represents either a hydrogen, fluorine or chlorine atom or a group $C_{1-6}$ alkyl, $C_{3-7}$ cycloalkyl, $C_{1-6}$ alkyloxy, $C_{1-6}$ alkylthio, $C_{1-6}$ fluoroalkyl or $C_{1-6}$ fluoroalkyloxy, $R_b$ represents a group $C_{1-6}$ alkyl, $C_{3-7}$ cycloalkyl or —$(CH_2)_n$—$C_{3-7}$ cycloalkyl, n represents 1, 2 or 3, p represents 0, 1 or 2, and also the pharmaceutically acceptable salts, solvates or hydrates thereof and the conformers or rotamers thereof.

The compounds of formula (I) may comprise one or more asymmetric carbon atoms. They may thus exist in the form of a mixture of enantiomers or of diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention. These salts are advantageously prepared with pharmaceutically acceptable acids, but the salts of other acids that are useful, for example for purifying or isolating the compounds of formula (I), also form part of the invention. These acids may be, for example, picric acid, oxalic acid or an optically active acid, for example a tartaric acid, a dibenzoyl-tartaric acid, a mandelic acid or a camphorsulfonic acid, and those that form physiologically acceptable salts, such as hydrochloride, hydrobromide, sulfate, hydrogen sulfate, dihydrogen phosphate, maleate, fumarate, 2-naphthalene-sulfonate or para-toluenesulfonate. For a review of physiologically acceptable salts, see the *Handbook of Pharmaceutical Salts: Properties, Selection and Use* by Stahl and Wermuth (Wiley-VCH, 2002).

The solvates or hydrates may be obtained directly after the synthetic process, compound (I) being isolated in the form of a hydrate, for example a monohydrate or hemihydrate, or of a solvate of the reaction or purification solvent.

The present invention includes the isotopically labelled pharmaceutically acceptable compounds of formula (I) in which one or more atoms are replaced with atoms having the same atomic number but an atomic mass or a mass number different from the atomic mass or the mass number that naturally predominates. Examples of isotopes that may be included in the compounds of the invention include hydrogen isotopes such as $^{2}H$ and $^{3}H$, carbon isotopes such as $^{11}C$, $^{13}C$ and $^{14}C$, chlorine isotopes such as $^{36}Cl$, fluorine isotopes such as $^{18}F$, iodine isotopes such as $^{123}I$ and $^{125}I$, nitrogen isotopes such as $^{13}N$ and $^{15}N$, oxygen isotopes such as $^{15}O$, $^{17}O$ and $^{18}O$, phosphorus isotopes such as $^{32}P$ and sulfur isotopes such as $^{35}S$. Substitutions with isotopes that emit positrons, such as $^{11}C$, $^{18}F$, $^{15}O$ and $^{13}N$, may be useful in Positron Emission Tomography studies for studying the occupation of receptors.

In the context of the invention, the following definitions apply:
- aryl: a monocyclic or bicyclic aromatic group containing 6 to 10 carbon atoms. Examples of aryl groups that may be mentioned include phenyl and naphthyl groups,
- $C_{b-c}$ in which b and c may take values from 1 to 6, a hydrocarbon-based chain of b to c carbon atoms, for example $C_{1-6}$ is a hydrocarbon-based chain that may contain from 1 to 6 carbon atoms,
- alkyl: a linear or branched saturated aliphatic group, for example a group $C_{1-6}$ alkyl represents a linear or branched hydrocarbon-based chain of 1 to 6 carbon atoms, for example a methyl, ethyl, n-propyl, isopropyl, n-butyl, isobutyl, tert-butyl, pentyl or hexyl,
- cycloalkyl: an optionally branched, cyclic saturated hydrocarbon-based chain containing from 3 to 7 carbon atoms, for example a cyclopropyl, cyclobutyl, cyclopentyl, cyclohexyl or cycloheptyl,
- alkyloxy: a group —O-alkyl,
- alkylthio: a group —S-alkyl,
- fluoroalkyl: an alkyl group in which one or more hydrogen atoms have been replaced with a fluorine,
- fluoroalkyloxy: an alkyloxy group in which one or more hydrogen atoms have been replaced with a fluorine atom.

According to the present invention, among the compounds of formula (I) as defined above, the ones that are particularly preferred are those that have one or a combination of the following characteristics:
- $R_1$ represents a methyl, ethyl or isopropyl group,
- $R_2$ represents a chlorine or bromine atom or a methyl, ethyl, isopropyl or tert-butyl group,
- $R_3$ represents a hydrogen atom,
- $R_4$ and $R_{4'}$ are either identical and represent a methyl, ethyl or propyl group, or the groups $R_4$ and $R_{4'}$ form with the carbon atom that bears them a cyclopentyl or cyclohexyl ring.

The compounds below, and the pharmaceutically acceptable salts, solvates and hydrates, and the conformers or rotamers thereof, are particularly preferred:
- 4-{3-[(2,6-diisopropylphenylcarbamoyl)methyl]-2,4-dioxo-1,3-diazaspiro[4.5]dec-1-yl}benzoic acid ethyl ester
- 2-[1-(4-cyanophenyl)-2,4-dioxo-1,3-diazaspiro[4.5]dec-3-yl]-N-(2,6-diisopropylphenyl)acetamide
- 2-[1-(3-cyano-4-methylphenyl)-2,4-dioxo-1,3-diaza-spiro[4.5]dec-3-yl]-N-(2,6-diisopropylphenyl)acetamide
- N-(2,6-diisopropylphenyl)-2-[1-(4-methylsulfanyl-phenyl)-2,4-dioxo-1,3-diazaspiro[4.5]dec-3-yl]acetamide
- N-(2,6-diisopropylphenyl)-2-[1-(4-methanesulfonyl-phenyl)-2,4-dioxo-1,3-diazaspiro[4.5]dec-3-yl]acetamide
- 4-{3-[(2,6-diisopropylphenylcarbamoyl)methyl]-2,4-dioxo-1,3-diazaspiro[4.5]dec-1-yl}benzoic acid methyl ester A subject of the invention is also a process for preparing the compounds of general formula (I).

In accordance with the invention, the compounds of formula (I) may be prepared according to the general process described in Scheme 1 below.

Scheme 1

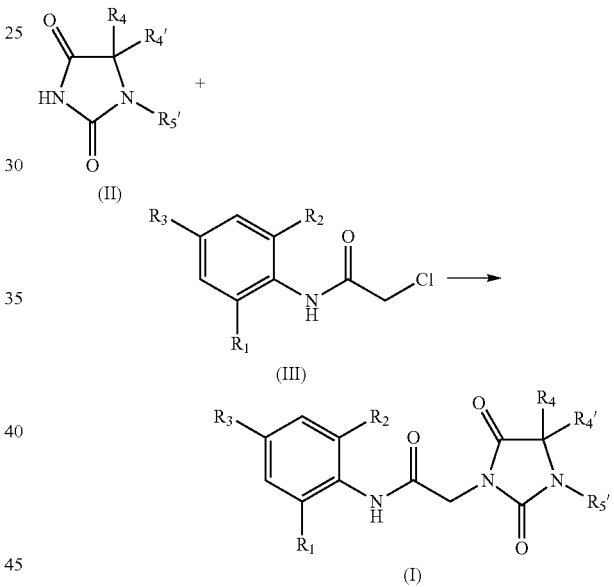

The compounds of formula (I) in which $R_1$, $R_2$, $R_3$, $R_4$, $R_{4'}$ and $R_5$ are as defined above may be prepared by reacting the dioxo-imidazolidines of formula (II) with the chloroacetamides of formula (III), in the presence of a base, according to Scheme 1 and by analogy, for example, with the reactions described by Dunbar, B. et al., *Pharmazie* 2002, 57 (7), 438, Pinza, M. et al., *J. Med. Chem.* 1993, 36 (26), 4214, Coudert, P. et al., *Pharm. Acta Helv.* 1991, 66 (5-6), 155 or Usifoh, C. O.; *Arch. Pharm.* 2001, 334 (11), 366. The group $R_{5'}$ represents either the group $R_5$ defined above or a precursor of $R_5$ converted into $R_5$ via a method known to those skilled in the art.

Synthesis of the Intermediates (II) and (III)

The dioxo-imidazolidines of general formula (II) in which $R_4$ and $R_{4'}$ are as defined above for the compounds of formula (I) and the group $R_{5'}$ represents either the group $R_5$ defined above for the compounds of formula (I) or a precursor of $R_5$ converted into $R_5$ via a method known to those skilled in the art. The dioxo-imidazolidines of general formula (II) may be prepared according to Scheme 2 below.

Scheme 2

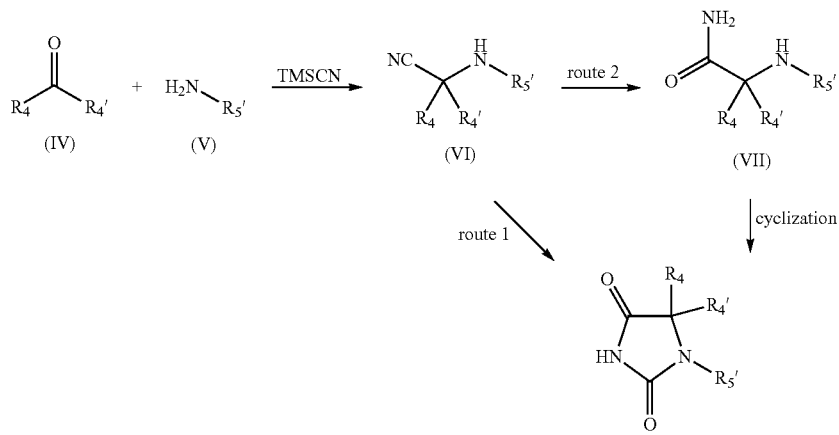

The nitrile compounds of formula (VI) are obtained from the ketones of formula (IV) reacted with the amines of formula (V) in the presence of trimethylsilyl cyanide, in accordance, for example, with the conditions described in Matsumoto K. et al., *Helv. Chim. Acta* 2005, 88 (7), 1734-1753 or Nieto M. J. et al., *J. Comb. Chem.* 2005, 7 (2), 258-263.

The ketones (IV) and the amines (V) are commercial compounds or are prepared according to techniques that are well known to those skilled in the art.

Scheme 2 Route 1

The dioxo-imidazolidine intermediates of formula (II) may be prepared by reacting the nitrile derivatives (VI) with potassium isocyanate, followed by work-up in acidic medium according, for example, to the conditions described in patent DE 1 032 258.

Scheme 2 Route 2

Hydrolysis of the nitrile function of the compounds of formula (VI) in the presence of acid, for example under the conditions described in Beths R. L. et al., *J. Chem. Soc.*, 1927, 1310, makes it possible to obtain the primary amides of formula (VII). Cyclization in the presence of a suitable aryl isocyanate as described in Papadopoulos, E. P.; *J. Org. Chem.* 1977, 42, 3925 makes it possible to obtain the dioxo-imidazolidines of formula (II).

The chloroacetamides of general formula (III) may be prepared by reaction between the anilines of formula (VIII) and chloroacetyl chloride in the presence of a base, for example as described in Davion, Y. et al., *Heterocycles* 2004, 63 (5), 1093 or in Juaristi, E. et al., *J. Org. Chem.* 1999, 64 (8), 2914, as illustrated in Scheme 3 below in which $R_1$, $R_2$ and $R_3$ are as defined for the compounds of formula (I):

Scheme 3

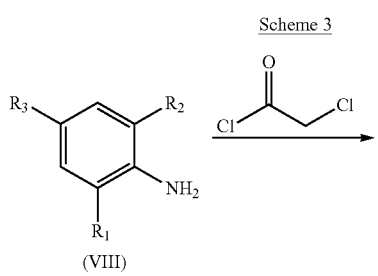

-continued

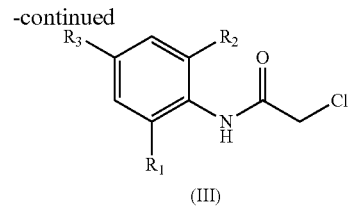

The functional groups that may be present in the reaction intermediates used in the process may be protected, either permanently or temporarily, with protecting groups that ensure an unequivocal synthesis of the expected compounds. The protection and deprotection reactions are performed according to techniques that are well known to those skilled in the art. The term "temporary protecting group for amines, alcohols or carboxylic acids" means protecting groups such as those described in "Protective Groups in Organic Chemistry", published by McOmie J. W. F., Plenum Press, 1973, in "Protective Groups in Organic Synthesis", 2nd edition, Greene T. W. and Wuts P. G. M., published by John Wiley & Sons, 1991, and in "Protecting Groups", Kocienski P. J., 1994, Georg Thieme Verlag.

The compounds (I) according to the invention, and also the pharmaceutically acceptable salts, solvates and/or hydrates thereof, have inhibitory properties on the enzyme SOAT-1. This inhibitory activity on the enzyme SOAT-1 is measured according to a HepG2 primary enzymatic test, as described in Example 7. The preferred compounds of the present invention have a concentration that enables inhibition of 50% of the response of the enzyme ($IC_{50}$) of less than or equal to 1000 nM, preferentially less than or equal to 300 nM and advantageously less than or equal to 50 nM.

A subject of the present invention is also, as medicaments, the compounds of formula (I) as described above, and also the pharmaceutically acceptable salts and pharmaceutically acceptable solvates and/or hydrates thereof.

A subject of the present invention is the use of at least one compound of formula (I), or pharmaceutically acceptable salts or solvates and/or hydrates thereof, for the manufacture of a medicament for preventing and/or treating sebaceous gland disorders such as hyperseborrhoea, acne, seborrhoeic dermatitis or atopic dermatitis, ocular pathologies such as blepharitis or meibomitis (disorder of the Meibomian gland) or pathologies such as hypercholesterolaemia, arteriosclerosis or Alzheimer's disease. The compounds according to the invention are particularly suitable for the manufacture of a pharmaceutical composition for treating acne. The compounds according to the invention are thus suitable for use in the pathologies listed above.

A subject of the present invention is also a pharmaceutical or cosmetic composition comprising, in a physiologically acceptable support, at least one compound of formula (I) as defined above, or a pharmaceutically acceptable salt or solvate and/or hydrate thereof. The compositions according to the invention thus comprise a physiologically acceptable support or at least one physiologically or pharmaceutically acceptable excipient, chosen according to the desired cosmetic or pharmaceutical form and the chosen mode of administration.

The term "physiologically acceptable support or medium" means a support that is compatible with the skin, mucous membranes and/or the integuments.

The administration of the composition according to the invention may be performed via the enteral, parenteral, rectal, topical or ocular route. Preferably, the pharmaceutical composition is conditioned in a form that is suitable for topical application.

Via the enteral route, the composition, more particularly the pharmaceutical composition, may be in the form of tablets, gel capsules, coated tablets, syrups, suspensions, solutions, powders, granules, emulsions, microspheres or nanospheres or lipid or polymer vesicles allowing controlled release. Via the parenteral route, the composition may be in the form of solutions or suspensions for perfusion or for injection.

The compositions according to the invention contain a compound according to the invention, in an amount sufficient to obtain the desired therapeutic, prophylactic or cosmetic effect. The compounds according to the invention are generally administered at a daily dose of about 0.001 mg/kg to 100 mg/kg of body weight, in 1 to 3 dosage intakes. The compounds are used systemically at a concentration generally of between 0.001% and 10% by weight and preferably between 0.01% and 2% by weight relative to the weight of the composition.

Via the topical route, the pharmaceutical composition according to the invention is more particularly intended for treating the skin and mucous membranes and may be in the form of ointments, creams, milks, pomades, powders, impregnated pads, syndets, solutions, gels, sprays, mousses, suspensions, lotions, sticks, shampoos or washing bases. It may also be in the form of suspensions of microspheres or nanospheres or lipid or polymer vesicles or polymer patches and hydrogels allowing controlled release. This topical composition may be in anhydrous form, in aqueous form or in the form of an emulsion.

The compounds are used topically at a concentration generally of between 0.001% and 10% by weight and preferably between 0.01% and 2% by weight relative to the total weight of the composition.

The compounds of formula (I) according to the invention and the pharmaceutically acceptable salts or solvates and/or hydrates thereof also find an application in the cosmetics field, in particular in body and hair hygiene and more particularly for combating or preventing greasy skin or hair or a greasy scalp.

A subject of the invention is thus also the cosmetic use of a composition comprising, in a physiologically acceptable support, at least one of the compounds of formula (I), optionally in the form of a pharmaceutically acceptable salt or solvate and/or hydrate, for body or hair hygiene.

The cosmetic composition according to the invention containing, in a cosmetically acceptable support, at least one compound of formula (I) or a pharmaceutically acceptable salt or solvate and/or hydrate thereof may especially be in the form of a cream, a milk, a lotion, a gel, an ointment, a pomade, a suspension of microspheres or nanospheres or lipid or polymer vesicles, impregnated pads, solutions, sprays, mousses, sticks, soaps, shampoos or washing bases.

The concentration of compound of formula (I) in the cosmetic composition is between 0.001% and 3% by weight relative to the total weight of the composition.

The pharmaceutical and cosmetic compositions as described previously may also contain inert or even pharmacodynamically active additives as regards the pharmaceutical compositions, or combinations of these additives, and especially:
wetting agents;
flavour enhancers;
preserving agents such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase, ubiquinol or certain metal-chelating agents;
emollients;
moisturizers, for instance glycerol, PEG-400, thiamorpholinone and derivatives thereof, or urea;
carotenoids and especially β-carotene;
α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and salts, amides or esters thereof.

Needless to say, a person skilled in the art will take care to select the optional compound(s) to be added to these compositions such that the advantageous properties intrinsically associated with the present invention are not, or are not substantially, adversely affected by the envisaged addition. Moreover, in general, the same preferences as those indicated previously for the compounds of formula (I) apply mutatis mutandis to the medicaments and cosmetic and pharmaceutical compositions and to the use using the compounds of the invention.

Several examples of preparation of active compounds of formula (I) according to the invention, and the results of the biological activity of such compounds, are given hereinbelow as illustrations and with no limiting nature.

PROCEDURES

Example 1

4-{3-[(2,6-Diisopropylphenylcarbamoyl)-methyl]-2,4-dioxo-1,3-diazaspiro[4.5]dec-1-yl}benzoic acid ethyl ester Step 1.1 4-(1-Cyanocyclohexylamino)benzoic acid ethyl ester Preparation According to Scheme 2

2 g (12.1 mmol, 1 eq.) of ethyl 4-aminobenzoate (Starting material 1) are added to a solution of 1.25 g (12.1 mmol, 1 eq.) of cyclohexanone (Starting material 2) in 20 ml of acetic acid at 0° C. The solution is stirred for 15 minutes, and 1.6 ml (12 mmol, 1 eq.) of trimethylsilyl cyanide are added. The reaction medium is stirred for 5 hours at room temperature. It is then poured gently into ice-cold ammonium hydroxide solution and extracted with ethyl acetate. The organic phases are combined and washed with water. They are dried over sodium sulfate. The residue is precipitated from dichloromethane and heptane. The product 4-(1-cyano-cyclohexylamino)benzoic acid ethyl ester is obtained in the form of a white solid.

Melting point=101-102° C.

Step 1.2 4-(1-Carbamoylcyclohexylamino)benzoic acid ethyl ester

Preparation According to Scheme 2, Route 2

550 mg (2.02 mmol) of 4-(1-cyanocyclohexylamino)-benzoic acid ethyl ester are dissolved in 20 ml of concentrated sulfuric acid. The reaction medium is stirred at room temperature for 5 hours. The reaction medium is poured gently onto ice, the pH is brought to 12 with sodium hydroxide, and the resulting mixture is extracted with ethyl acetate. The organic phases are combined and washed with water. They are dried over sodium sulfate. The solvents are evaporated off. The product is chromatographed on silica gel (60/40 heptane/ethyl acetate). The product 4-(1-carbamoyl-cyclohexylamino)benzoic acid ethyl ester is obtained in the form of a white solid.

Melting point=155-157° C.

Step 1.3
4-(2,4-Dioxo-1,3-diazaspiro[4.5]dec-1-yl)benzoic acid ethyl ester

Preparation According to Scheme 2 Route 2, Cyclization Step

380 μl (1.85 mmol, 1.2 eq.) of 2,6-diisopropylphenyl isocyanate are added to a solution of 450 mg (1.55 mmol, 1 eq.) of 4-(1-carbamoyl-cyclohexylamino)benzoic acid ethyl ester in 15 ml of toluene. The reaction medium is stirred at 180° C. for 2 hours with microwave irradiation. The toluene is evaporated off and the residue is purified on silica gel (heptane/ethyl acetate). The product 4-(2,4-dioxo-1,3-diazaspiro[4.5]dec-1-yl)benzoic acid ethyl ester is obtained in the form of a white solid.

Melting point=223-225° C.

Step 1.4 4-{3-[(2,6-Diisopropylphenylcarbamoyl)-methyl]-2,4-dioxo-1,3-diazaspiro[4.5]dec-1-yl}benzoic acid ethyl ester Synthesis According to Scheme 1

87 mg (0.63 mmol, 1 eq.) of potassium carbonate are added to a solution of 200 mg (0.63 mmol, 1 eq.) of 4-(2,4-dioxo-1,3-diazaspiro[4.5]dec-1-yl)benzoic acid ethyl ester and 160 mg (0.63 mmol, 1 eq.) of 2-chloro-N-(2,6-diisopropylphenyl)acetamide in 30 ml of dimethylformamide. The reaction medium is stirred at room temperature overnight. It is then poured into water and extracted with ethyl acetate. The organic phases are combined and washed with water. They are dried over sodium sulfate. The solvents are evaporated off. The residue is precipitated from dichloromethane and heptane. The product 4-{3-[(2,6-diisopropyl-phenylcarbamoyl)methyl]-2,4-dioxo-1,3-diaza-spiro[4.5]dec-1-yl}benzoic acid ethyl ester is obtained in the form of a white solid.

Melting point=210-212° C.

NMR (CDCl$_3$) 1 (m, 1H); 1.18-1.3 (m, 12H); 1.39-1.45 (m, 3H); 1.56-1.75 (m, 5H); 2.04-2.15 (m, 4H); 3.07-3.39 (m, 2H); 3.92-4.49 (m, 4H); 6.79-7.42 (m, 6H); 8.13-8.17 (m, 2H)

Preparation of the intermediate
2-chloro-N-(2,6-diisopropylphenyl)acetamide

Synthesis According to Scheme 3

222 mL (1.59 mol) of triethylamine are added to a solution of 300 mL (1.59 mol) of 2,6-diisopropyl-phenylamine (Starting material 3) in 1 litre of dichloromethane. The reaction mixture is cooled to 0° C., and 127 mL (1.59 mol) of chloroacetyl chloride are then added dropwise. Once the addition is complete, the ice bath is removed and the medium is stirred for 20 minutes. It is then poured into water and extracted with dichloromethane. The organic phases are combined and washed with water. They are dried over sodium sulfate. The solvents are evaporated off. The residue is filtered through silica gel (eluent: dichloromethane). The filtrate is evaporated and then triturated in heptane. 2-Chloro-N-(2,6-diisopropylphenyl)acetamide is obtained in the form of a white solid.

Melting point=146-148° C.

Example 2

2-[1-(4-Cyanophenyl)-2,4-dioxo-1,3-diaza-spiro[4.5]dec-3-yl]-N-(2,6-diisopropylphenyl)acetamide Step 2.1
1-(4-Iodophenylamino)cyclohexanecarbonitrile Preparation According to Scheme 2

3 g (13.7 mmol, 1 eq.) of 4-iodoaniline are added to a solution of 1.4 ml (13.5 mmol, 1 eq.) of cyclohexanone in 20 ml of acetic acid at 0° C. The solution is stirred for a moment, and 1.8 ml (13.5 mmol, 1 eq.) of trimethylsilyl cyanide are added. The reaction medium is stirred overnight at room temperature. It is then poured gently into ice-cold ammonium hydroxide solution and extracted with dichloromethane. The organic phases are combined and washed with water. They are dried over sodium sulfate. The solvents are evaporated off and the residue is then chromatographed on silica gel. The product 1-(4-iodophenylamino)cyclohexanecarbonitrile is obtained in the form of a white solid.

Melting point=101-103° C.

Step 2.2 1-(4-iodophenyl)-1,3-diaza-spiro[4.5]decane-2,4-dione

Preparation According to Scheme 2, Route 1

1.8 g (22.2 mmol, 2 eq.) of potassium cyanate are added at 30° C. to a solution of 3.7 g (11.3 mmol, 1 eq.) of 1-(4-iodophenylamino)cyclohexanecarbonitrile in 30 ml of glacial acetic acid. The reaction medium is stirred at 60° C. overnight. 5 ml of hydrochloric acid and then 3 ml of water are added. The medium is heated at 90° C. for 1 hour and then at room temperature for 3 hours. Water is then poured into the reaction medium, and the precipitate formed is filtered off and then chromatographed on silica gel (50/50 heptane/ethyl acetate). 180 mg of 1-(4-iodophenyl)-1,3-diaza-spiro[4.5]decane-2,4-dione are obtained in the form of an orange-coloured solid.

Melting point=249-51° C.

Step 2.3 N-(2,6-diisopropylphenyl)-2-[1-(4-iodophenyl)-2,4-dioxo-1,3-diazaspiro[4.5]dec-3-yl]-acetamide Preparation According to Scheme 1
This compound is prepared according to the procedure described in step 1.4 above, starting with 1-(4-iodophenyl)-1,3-diazaspiro[4.5]decane-2,4-dione.

Melting point=262-264° C.

Step 2.4 2-[1-(4-Cyanophenyl)-2,4-dioxo-1,3-diazaspiro[4.5]dec-3-yl]-N-(2,6-diisopropylphenyl)acetamide According to the method described in: J. Org. Chem., 1998, 63, 8224-8228.

38 mg (0.58 mmol, 2 eq.) of potassium cyanide and 5.5 mg (0.029 mmol, 0.1 eq.) of copper iodide are added to 170 mg (0.29 mmol, 1 eq.) of N-(2,6-diisopropyl-phenyl)-2-[1-(4-iodo-phenyl)-2,4-dioxo-1,3-diaza-spiro[4.5]dec-3-yl]acetamide in 10 ml of tetrahydrofuran. The reaction medium is degassed with nitrogen for 20 minutes, and 17 mg (0.015 μmol, 0.05 eq.) of tetrakis(triphenylphosphine)palladium are added. The medium is heated at 80° C. for 6 hours. The medium is cooled to room temperature and diluted with ethyl acetate, and then filtered through Celite. The filtrate is washed with water. The organic phases are combined. They are dried over sodium sulfate. The solvents are evaporated off and the residue is precipitated from dichloromethane and heptane. The product 2-[1-(4-cyanophenyl)-2,4-dioxo-1,3-diazaspiro[4.5]dec-3-yl]-N-(2,6-diisopropylphenyl)acetamide is obtained in the form of a white solid.

Melting point=280-282° C.

$^1$H NMR (DMSO) 0.97-1.00 (m, 1H); 1.06-1.08 (d, 6H); 1.12-1.13 (d, 6H); 1.44-1.56 (m, 5H); 1.86-1.96 (m, 2H); 1.99-2.03 (m, 2H); 3.01-3.09 (m, 2H); 4.31 (s, 2H); 7.14-7.16 (d, 2H, J=7.68 Hz); 7.24-7.27 (m, 1H); 7.51-7.53 (d, 2H, J=8.44 Hz); 7.97-7.99 (d, 2H, J=8.44 Hz); 9.54 (s, 1H).

Example 5

N-(2,6-Diisopropylphenyl)-2-[1-(4-methanesulfonylphenyl)-2,4-dioxo-1,3-diaza-spiro[4.5]dec-3-yl]acetamide 0.421 g (0.684 mmol; 2.2 eq.) of oxone is added to a solution of 0.158 g (0.311 mmol; 1 eq.) of N-(2,6-diisopropylphenyl)-2-[1-(4-methylsulfanylphenyl)-2,4-dioxo-1,3-diazaspiro[4.5]dec-3-yl]acetamide (prepared according to Example 2) in 5 ml of methanol and 2 ml of demineralized water. The reaction medium is stirred at room temperature for 18 hours. Water and dichloromethane are added, and the organic phase is washed several times with water, dried over sodium sulfate and then concentrated to dryness. The product N-(2,6-diisopropylphenyl)-2-[1-(4-methanesulfonyl-phenyl)-2,4-dioxo-1,3-diazaspiro[4.5]dec-3-yl]acetamide is obtained in the form of a solid.

Melting point=250° C.

$^1$H NMR (DMSO): 9.55 (1H, s); 8.05 (2H, d, J=8.6 Hz); 7.58 (2H, d, J=8.6 Hz); 7.28-7.24 (1H, m); 7.15 (2H, d, J=7.68 Hz); 4.32 (2H, s); 3.30 (3H, s); 3.11-3.04 (2H, m); 2.05-2.01 (2H, m); 1.97-1.88 (2H, m); 1.58-1.45 (5H, m); 1.12-1.07 (12H, m); 0.98-0.94 (1H, m)

Example 6

4-{3-[(2,6-Diisopropylphenylcarbamoyl)-methyl]-2,4-dioxo-1,3-diazaspiro[4.5]dec-1-yl}benzoic acid methyl ester 33 mg of 4-{3-[(2,6-diisopropylphenylcarbamoyl)-methyl]-2,4-dioxo-1,3-diazaspiro[4.5]dec-1-yl}benzoic acid ethyl ester are dissolved in 10 ml of methanol, 1 drop of concentrated sulfuric acid is added and the solution is refluxed for 18 hours. The mixture is stirred at reflux for 72 hours. The solvent is evaporated off. The residue is dissolved in DCM, heptane is added until slight cloudiness appears, and the solution is stirred at room temperature under nitrogen for 16 hours. The product 4-{3-[(2,6-diisopropylphenylcarbamoyl)methyl]-2,4-dioxo-1,3-diaza-spiro[4.5]dec-1-yl}benzoic acid methyl ester is obtained in the form of fine white needles.

NMR (DMSO) 0.88-1.29 (m, 13H); 1.45-1.57 (m, 5H); 1.87-2.03 (m, 4H); 3.02-3.12 (m, 2H); 3.88 (s, 3H); 4.31 (s, 2H); 7.15 (d, 2H); 7.26 (t, 1H); 7.45 (d, 2H); 8.06 (d, 2H); 9.55 (s, 1H)

Examples 3 and 4

Examples 3 and 4 are described in Table 1 below. The compounds are synthesized according to the procedures described above, replacing the starting materials 1, 2 and 3 mentioned in Examples 1, 2, 5 and 6 with the products mentioned in Table 1.

TABLE 1

| Example # | IUPAC name | Starting material 1 | Starting material 2 | Starting material 3 | Synthetic route Scheme 2 | Melting point (° C.) | $^1$H NMR - 400 MHz (s = singlet, d = doublet, t = triplet, m = multiplet, q = quartet, J = coupling constant in Hz) |
|---|---|---|---|---|---|---|---|
| 1 | 4-{3-[(2,6-diisopropyl-phenylcarbamoyl)-methyl]-2,4-dioxo-1,3-diaza-spiro[4.5]dec-1-yl}-benzoic acid ethyl ester | Ethyl 4-aminobenzoate | cyclohexanone | 2,6-diisopropyl-phenyl-amine | route 2 | 210-212 | (CDCl$_3$) 1 (m, 1H); 1.18-1.3 (m, 12H); 1.39-1.45 (m, 3H); 1.56-1.75 (m, 5H); 2.04-2.15 (m, 4H); 3.07-3.39 (m, 2H); 3.92-4.49 (m, 4H); 6.79-7.42 (m, 6H); 8.13-8.17 (m, 2H); |
| 2 | 2-[1-(4-cyanophenyl)-2,4-dioxo-1,3-diaza-spiro[4.5]dec-3-yl]-N-(2,6-diisopropyl-phenyl)acetamide | 4-iodoaniline | cyclohexanone | 2,6-diisopropyl-phenyl-amine | route 1 | 280-282 | (DMSO) 0.97-1.00 (m, 1H); 1.06-1.08 (d, 6H); 1.12-1.13 (d, 6H); 1.44-1.56 (m, 5H); 1.86-1.96 (m, 2H); 1.99-2.03 (m, 2H); 3.01-3.09 (m, 2H); 4.31 (s, 2H); 7.14-7.16 (d, 2H, J = 7.68 Hz); 7.24-7.27 (m, 1H); 7.51-7.53 (d, 2H, J = 8.44 Hz); 7.97-7.99 (d, 2H, J = 8.44 Hz); 9.54 (s, 1H) |

TABLE 1-continued

| Example # | IUPAC name | Starting material 1 | Starting material 2 | Starting material 3 | Synthetic route Scheme 2 | Melting point (° C.) | $^1$H NMR - 400 MHz (s = singlet, d = doublet, t = triplet, m = multiplet, q = quartet, J = coupling constant in Hz) |
|---|---|---|---|---|---|---|---|
| 3 | 2-[1-(3-cyano-4-methylphenyl)-2,4-dioxo-1,3-diaza-spiro[4.5]dec-3-yl]-N-(2,6-diisopropyl-phenyl)acetamide | 5-amino-2-methyl-benzonitrile | cyclohexanone | 2,6-diisopropyl-phenyl-amine | route 1 | 231-233 | (DMSO) 0.95-1.01 (m, 1H); 1.08 (s, 6H); 1.12 (s, 6H); 1.39-1.45 (m, 2H); 1.56 (m, 3H); 1.85-1.91 (m, 2H); 1.99-2.02 (m, 2H); 2.53 (s, 3H); 3.03-3.09 (m, 2H); 4.29 (s, 2H); 7.14-7.16 (d, 2H, J = 7.6 Hz); 7.24-7.27 (m, 1H); 7.50-7.53 (dd, 1H, J = 6.28 Hz, J' = 2 Hz); 7.58-7.60 (d, 1H, J = 8.24 Hz); 7.74-7.75 (d, 1H, J = 1.84 Hz); 9.51 (s, 1H) |
| 4 | N-(2,6-diisopropyl-phenyl)-2-[1-(4-methylsulfanyl-phenyl)-2,4-dioxo-1,3-diaza-spiro[4.5]dec-3-yl]-acetamide | 4-(methyl-thio)aniline | cyclohexanone | 2,6-diisopropyl-phenyl-amine | route 1 | 210 | DMSO: 9.52 (1H, s); 7.35 (2H, d, J = 8.50 Hz); 7.27-7.23 (1H, m); 7.18 (2H, d, J = 8.50 Hz); 7.16-7.14 (2H, m); 4.28 (2H, s); 3.12-3.01 (2H, m); 2.50 (3H, s); 1.98-1.85 (4H, m); 1.56-1.53 (3H, m); 1.46-1.39 (2H, m); 1.12-1.09 (12H, m); 0.99-0.89 (1H, m) |
| 5 | N-(2,6-diisopropyl-phenyl)-2-[1-(4-methanesulfonyl-phenyl)-2,4-dioxo-1,3-diazaspiro-[4.5]dec-3-yl]-acetamide | 4-(methyl-thio)aniline | cyclohexanone | 2,6-diisopropyl-phenyl-amine | route 1 | 250 | (DMSO): 9.55 (1H, s); 8.05 (2H, d, J = 8.6 Hz); 7.58 (2H, d, J = 8.6 Hz); 7.28-7.24 (1H, m); 7.15 (2H, d, J = 7.68 Hz); 4.32 (2H, s); 3.30 (3H, s); 3.11-3.04 (2H, m); 2.05-2.01 (2H, m); 1.97-1.88 (2H, m); 1.58-1.45 (5H, m); 1.12-1.07 (12H, m); 0.98-0.94 (1H, m) |
| 6 | 4-{3-[(2,6-diisopropyl-phenylcarbamoyl)-methyl]-2,4-dioxo-1,3-diaza-spiro[4.5]dec-1-yl}-benzoic acid methyl ester | Ethyl 4-aminobenzoate | cyclohexanone | 2,6-diisopropyl-phenyl-amine | route 2 | — | (DMSO) 0.88-1.29 (m, 13H); 1.45-1.57 (m, 5H); 1.87-2.03 (m, 4H); 3.02-3.12 (m, 2H); 3.88 (s, 3H); 4.31 (s, 2H); 7.15 (d, 2H); 7.26 (t, 1H); 7.45 (d, 2H); 8.06 (d, 2H); 9.55 (s, 1H) |

All the NMR (nuclear magnetic resonance) spectra are in accordance with the proposed structures. The chemical shifts are expressed in parts per million. The internal reference is tetramethylsilane. The following abbreviations are used: CDCl$_3$=deuterated chloroform, DMSO=deuterated dimethyl sulfoxide

Example 7

Biological Tests

The compounds of formula (I) according to the invention were subjected to a test for evaluating their inhibitory activity towards the enzyme ACAT-1, inspired by the following publication: "Identification of ACAT1- and ACAT2-specific inhibitors using a novel, cell based fluorescence assay: individual ACAT uniqueness", J. Lipid. Res. (2004) vol. 45, pages 378-386.

The principle of this test is based on the use of NBD-cholesterol, a cholesterol analogue whose fluorescence depends on its environment. When this molecule is in a polar environment, it is weakly fluorescent, whereas in a non-polar environment it is strongly fluorescent. Free NBD-cholesterol becomes inserted in cell membranes and is weakly fluorescent in this polar environment. When NBD-cholesterol is esterified with ACAT, the NBD-cholesterol ester enters non-polar lipid droplets and is then strongly fluorescent.

The method below is applied: HepG2 cells are incubated in the presence of NBD-cholesterol (1 µg/ml) and of the test compound of formula (I) in black transparent-bottomed 96-well plates, at a rate of 30 000 cells per well. After incubation for 6 hours at 37° C. under 5% CO$_2$, the medium is removed by turning upside-down and the cells are washed with twice 100 µl of PBS. After addition of 50 µl of lysis buffer (10 mM NaPO$_4$, 1% Igepal), the plates are shaken for 5 minutes and the fluorescence is read (excitation at 490 nm, emission at 540 nm) on a Fusion machine (Perkin-Elmer). By way of illustration, an IC$_{50}$ of 2.4 nM is obtained for compound (1), an IC$_{50}$ of 77 nM is obtained for compound (2), an IC$_{50}$ of 2.5 nM is obtained for compound (3), an IC$_{50}$ of 1.5 nM is obtained for compound (4) and an IC$_{50}$ of 31 nM is obtained for compound (5).

Example 8

Formulations

Various formulations containing the compounds according to the invention are given below.

A—Oral Route
(a) 0.2 g tablet

| | |
|---|---|
| Compound 1 | 0.01 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml vials

| | |
|---|---|
| Compound 3 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavouring | qs |
| Purified water | qs 5 ml |

B—Topical Route
(a) Ointment

| | |
|---|---|
| Compound 2 | 0.300 g |
| White petroleum jelly codex | qs 100 g |

(d) Lotion

| | |
|---|---|
| Compound 4 | 0.100 g |
| Polyethylene glycol (PEG 400) | 69.900 g |
| 95% Ethanol | 30.000 g |

(e) Hydrophobic ointment

| | |
|---|---|
| Compound 1 | 0.300 g |
| Isopropyl myristate | 36.400 g |
| Silicone oil (Rhodorsil 47 V 300) | 36.400 g |
| Beeswax | 13.600 g |
| Silicone oil (Abil 300 000 cSt) | qs 100 g |

(f) Nonionic oil-in-water cream

| | |
|---|---|
| Compound 6 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

The invention claimed is:

1. A compound of formula (I):

in which:
R1 represents a group $C_{1-6}$ alkyl, $C_{3-7}$ cycloalkyl, $C_{1-6}$ alkyloxy, $C_{1-6}$ fluoroalkyl or $C_{1-6}$ fluoroalkyloxy or a group —$(CH_2)_n$—$C_{3-7}$ cycloalkyl, R2 and R3 are identical or different and represent a hydrogen, fluorine, chlorine, bromine or iodine atom or a group $C_{1-6}$ alkyl, $C_{3-7}$ cycloalkyl, $C_{1-6}$ alkylthio, $C_{1-6}$ alkyloxy, $C_{1-6}$ fluoroalkyl or $C_{1-6}$ fluoroalkyloxy or a group —$(CH_2)_n$—$C_{3-7}$ cycloalkyl, R4 and $R_4'$ are identical or different and represent a group $C_{3-7}$ cycloalkyl, a group —$(CH_2)_n$—$C_{3-7}$ cycloalkyl or a group $C_{1-6}$ alkyl optionally substituted with one to three groups $R_a$, or the groups R4 and $R_4'$ form, with the carbon atom that bears them, a ring $C_{1-6}$ alkyl, R5 represents a group selected from the group consisting of:
a phenyl group substituted with at least one, two or three identical or different substituents selected from the group consisting of $S(O)_p$, $COOR_b$ and CN and optionally accompanied by a group Ra,
a group —$(CH_2)_n$-aryl, the aryl group being substituted with one or more groups $S(O)_p$, $COOR_a$ or CN, $R_a$ represents either a hydrogen, fluorine or chlorine atom or a group $C_{1-6}$ alkyl, $C_{3-7}$ cycloalkyl, $C_{1-6}$ alkyloxy, $C_{1-6}$ alkylthio, $C_{1-6}$ fluoroalkyl or $C_{1-6}$ fluoroalkyloxy, $R_b$ represents a group $C_{1-6}$ alkyl, $C_{3-7}$ cycloalkyl or —$(CH_2)_n$—$C_{3-7}$ cycloalkyl, n represents 1, 2 or 3,
p represents 0, 1 or 2, or a pharmaceutically acceptable salts, solvate or hydrate thereof or a conformer or rotamer thereof.

2. The compound according to claim 1, wherein:
R1 represents a methyl, ethyl or isopropyl group,
R2 represents a chlorine or bromine atom or a methyl, ethyl, isopropyl or tert-butyl group,
R3 represents a hydrogen atom,
R4 and $R_4'$ are either identical and represent a methyl, ethyl or propyl group, or the groups R4 and $R_4'$ form with the carbon atom that bears them a cyclopentyl or cyclohexyl ring;
or a pharmaceutically acceptable salt, solvate, hydrate, conformer or rotamer thereof.

3. The compound according to claim 1, selected from the group consisting of:
4-{3-[(2,6-diisopropylphenylcarbamoyl)methyl]-2,4-dioxo-1,3-diazaspiro[4.5]dec-1-yl}benzoic acid ethyl ester;
2-[1-(4-cyanophenyl)-2,4-dioxo-1,3-diazaspiro[4.5]dec-3-yl]-N-(2,6-diisopropylphenyl)acetamide;

2-[1-(3-cyano-4-methylphenyl)-2,4-dioxo-1,3-diazaspiro[4.5]dec-3-yl]-N-(2,6-diisopropylphenyl)acetamide;

N-(2,6-diisopropylphenyl)-2-[1-(4-methylsulfanylphenyl)-2,4-dioxo-1,3-diazaspiro[4.5]dec-3-yl]acetamide;

N-(2,6-diisopropylphenyl)-2-[1-(4-methanesulfonylphenyl)-2,4-dioxo-1,3-diazaspiro[4.5]dec-3-yl]acetamide; and 4-{3-[(2,6-diisopropylphenylcarbamoyl)methyl]-2,4-dioxo-1,3-diazaspiro[4.5]dec-1-yl}benzoic acid methyl ester;

or a pharmaceutically acceptable salt, solvate, hydrate, conformer or rotamer thereof.

4. A pharmaceutical composition comprising, in a physiologically acceptable support, at least one compound of formula (I) according to claim 1 or a pharmaceutically acceptable salt, solvate, hydrate, conformer or rotamer thereof.

5. The composition according to claim 4, wherein the concentration of the compound of formula (I) is between 0.001% and 10% by weight relative to the total weight of the composition.

6. The composition according to claim 5, wherein the concentration of the compound of formula (I) is between 0.01% and 2% by weight relative to the total weight of the composition.

7. A cosmetic composition, comprising, in a physiologically acceptable support, at least one compound of formula (I) according to claim 1.

8. The composition according to claim 7, wherein the concentration of the compound of formula (I) is between 0.001% and 3% by weight relative to the total weight of the composition.

9. The composition according to claim 1, wherein it is in a form suitable for topical application.

10. The composition according to claim 9, wherein the composition is in the form of a cream, a milk, a lotion, a gel, an ointment, a pomade, a suspension of microspheres or nanospheres or lipid or polymer vesicles, an impregnated pad, a solution, a spray, a mousse, a stick, a soap, a shampoo or a washing base.

11. A cosmetic method, the method comprising administering a composition as defined in claim 9 to an individual subject in need, for body or hair hygiene.

12. A method for the treatment of a sebaceous gland disorder, an ocular pathology, hypercholesterolaemia or arteriosclerosis, said method comprising administering to an individual subject in need of such treatment an effective amount of a pharmaceutical composition according to claim 4.

13. A method for the treatment of acne, said method comprising administering to an individual subject in need of such treatment an effective amount of a pharmaceutical composition according to claim 4.

14. A method for the treatment of a sebaceous gland disorder selected from the group consisting of hyperseborrhoea, acne, seborrhoeic dermatitis and atopic dermatitis, said method comprising administering to an individual subject in need of such treatment an effective amount of a pharmaceutical composition according to claim 4.

15. A method for the treatment of an ocular pathology selected from the group consisting of blepharitis and meibomitos, said method comprising administering to an individual subject in need of such treatment an effective amount of pharmaceutical composition according to claim 4.

16. A pharmaceutical composition comprising, in a physiologically acceptable support, at least one compound of formula (I) according to claim 2, or a pharmaceutically acceptable salt, solvate, hydrate, conformer or rotamer thereof.

17. A pharmaceutical composition comprising, in a physiologically acceptable support, at least one compound of formula (I) according to claim 3, or a pharmaceutically acceptable salt, solvate, hydrate, conformer or rotamer thereof.

18. A method for the treatment of acne, said method comprising administering to an individual subject in need of such treatment an effective amount of a pharmaceutical composition according to claim 16.

19. A method for the treatment of acne, said method comprising administering to an individual subject in need of such treatment an effective amount of a pharmaceutical composition according to claim 17.

20. A method for the treatment of a sebaceous gland disorder selected from the group consisting of hyperseborrhoea, acne, seborrhoeic dermatitis and atopic dermatitis, said method comprising administering to an individual subject in need of such treatment an effective amount of a pharmaceutical composition according to claim 16.

21. A method for the treatment of a sebaceous gland disorder selected from the group consisting of hyperseborrhoea, acne, seborrhoeic dermatitis and atopic dermatitis, said method comprising administering to an individual subject in need of such treatment an effective amount of a pharmaceutical composition according to claim 17.

22. A method for the treatment of an ocular pathology selected from the group consisting of blepharitis and meibomitos, said method comprising administering to an individual subject in need of such treatment an effective amount of pharmaceutical composition according to claim 16.

23. A method for the treatment of an ocular pathology selected from the group consisting of blepharitis and meibomitos, said method comprising administering to an individual subject in need of such treatment an effective amount of pharmaceutical composition according to claim 17.

* * * * *